United States Patent [19]

Wallach et al.

[11] Patent Number: 5,211,945
[45] Date of Patent: May 18, 1993

[54] COMPOSITIONS AND METHODS FOR MODULATING THE EFFECT OF TNF AND IL-1

[75] Inventors: David Wallach, Rehovot, Israel; Helmut Holtmann, Porta Westfalica, Fed. Rep. of Germany

[73] Assignee: Yeda Research and Development Co. Ltd., Rehovot, Israel

[21] Appl. No.: 94,981

[22] Filed: Sep. 9, 1987

[30] Foreign Application Priority Data

Sep. 10, 1986 [IL] Israel ......................................... 80005

[51] Int. Cl.$^5$ ............................................. A61K 37/02
[52] U.S. Cl. ................................. 424/85.1; 424/85.2; 424/85.4; 424/85.5; 424/85.6; 424/85.7; 514/2; 514/8; 514/885
[58] Field of Search ........................... 424/85.1-85.7; 514/2, 8, 885

[56] References Cited

U.S. PATENT DOCUMENTS 4,863,727  9/1989  Zimmerman et al. ............. 424/85.2
4,879,111  11/1989  Chong ............................... 424/85.1
4,948,875  8/1990  Tanaka et al. ...................... 530/350
4,980,160  12/1990  Goldberg et al. .................... 530/351

OTHER PUBLICATIONS

Beutler et al, Science, 229, 1985, pp. 869-871.
Moore et al, PNAS, 84, 1987, pp. 7134-7138.
Santoli et al, J Immunol, 139, 1987, pp. 3348-3354.
Beutler et al, Nature, 320, 1985, pp. 584-588.
Immune Modulation Agents and Their Mechanisms, ed Fenichel et al, 1984 (index only).
Philip, Nature, 323, 1986, pp. 86-89.
Old, Nature 326 1987, pp. 330-331.
Neta et al, J Immunol 136(7) 1986, p. 2483.
Itano et al, CA vol. 108, 1988, #15896u.
Seelentag et al EMBO Journal 1987, pp. 2261-2265.
Bachwich et al BBRC 136, 1986, pp. 94-101.
Kawakami et al BBRC 141, 1986, pp. 482-487.
Ghiara et al, J Immunol, vol. 139, 1987, pp. 3676-3679.
Wallach, "Cytotoxins (Tumour Necrosis Factor, Lymphotoxin and Others): Molecular and Functional Characteristics and Interactions with Interferons", Interferon 7 (ed. Gresser), pp. 89-124 (1986, Academic Press, London).
Israel et al "Binding of Human TNF-α to High-Affinity Cell Surface Receptors: Effect of IFN", Immunology Letters, 12:217-27 (1986).
Wallach, "Preparations of Lymphotoxin Induce Resistance to Their Own Cytotoxic Effect", T. Immunology 132:2464-69 (1984).

Primary Examiner—Garnette D. Draper

[57] ABSTRACT

This invention relates to methods for modulating the effects of TNF and IL-1, both the deleterious and the therapeutical effect of these cytokines. In case of deleterious effects, the invention provides methods for modulating the deleterious effect of TNF and/or IL-1 in mammals, by administering to a mammal sub-deleterious amounts of TNF and/or IL-1. The TNF and/or IL-1 to be modulated may be endogenous, i.e. generated in the organism in severe cases in amounts deleterious to the organism, or exogenously administered to a patient in amounts which are potentially deleterious. The compositions of the invention comprise effective amounts of TNF and/or IL-1 with at least one pharmaceutically acceptable carrier. The invention also relates to methods for monitoring the modulation of the TNF effect in patients treated with TNF and/or IL-1.

11 Claims, 13 Drawing Sheets

COMPOSITIONS AND METHODS FOR MODULATING THE EFFECT OF TNF AND IL-1

FIELD OF THE INVENTION

The present invention relates to methods for modulating the effect of TNF and IL-1 in mammals, and to methods for monitoring the modulation of the TNF effect in mammals. The invention also relates to compositions comprising effective amounts of TNF and IL-1.

BACKGROUND OF THE INVENTION

The structures of tumor necrosis factor (TNF) and of interleukin-1 (IL-1), as indicated by their amino acid sequences (1-6) bare no similarity to each other. However, recent information on the function of these cytokines suggests that their mechanisms of action are closely related. TNF-alpha and the structurally homologous lymphokine, lymphotoxin, also named TNF-beta, were initially identified by their ability to mediate in vitro cytotoxic effects on some cultured tumor cells and to induce in mice hemorrhagic necrosis in certain transplantable tumors (7-9). Yet, it has later been found that TNF exerts, besides cytotoxic activity, many other effects of the quite heterogeneous nature on cell functions (10). Several of these effects appear indistinguishable from those of IL-1. Both TNF and IL-1 have been found, for example, to stimulate the growth of fibroblasts and to induce in these cells the synthesis of collagenase, prostaglandin $E_2$ and interferon beta-2 (11-16), to decrease in adipocytes the activity of lipoprotein lipase (17, 18), to activate osteoclasts (19, 20), and to increase in endothelial cells adhesivity for blood leukocytes and synthesis of a cell surface protein which is probably involved in that adherence (21-23). Like TNF, IL-1 is cytotoxic to some tumor cells (24).

Among the many possible effects of the cytotoxins (CTXs), no doubt the one with the most far-reaching bearing on functioning of the cell is cell death, resulting from the cytotoxic activity of the CTXs. Cells treated by interferons (IFNs) are found to exhibit a significant increase in vulnerability to killing by the CTXs (10, 30) due to an increase in TNF receptor expression induced in those cells by IFNs (28, 30, 33, 34). There are several indications that vulnerability to the cytotoxic effect is subjected to regulation by mechanisms which, at least in part, are independent to those controlling the response to other effects of CTXs. Thus, comparison of effects of the CTXs on cells of different cultured lines has revealed marked differences in vulnerability from one cell line to another; tumor cells being in general more vulnerable than normal ones. These differences did not correlate to the level of receptors to the CTXs, nor to the effectiveness at which non cytotoxic effects could be induced in the cells. Cell killing by the CTXs is enhanced not only by IFNs, but also by metabolic blockers, such as inhibitors of RNA and protein synthesis (10). Prior art relating to the fact that TNF and IL-1 function through binding to high affinity cell surface receptors is disclosed in references (26) to (32).

Inhibitors of RNA and protein synthesis, sensitize certain cells to the cytotoxic effect of tumor necrosis factor (TNF). Treating cells with TNF, for a few hours, in the absence of such inhibition decreases the sensitivity to killing by subsequent application of TNF together with the inhibitors. Such decrease in vulnerability to killing by TNF could be observed also when treating cells with preparations of leukocyte-produced cytokines which were effectively depleted of TNF and lymphotoxin activity (10).

It is thus known that TNF has a cytocidal activity against tumor cells in culture. It is further known that the killing by TNF is markedly potentiated by sensitizing agents, particularly by agents inhibiting the synthesis of RNA and of proteins, i.e. metabolic blockers. Thus, such sensitizing agents increase the vulnerability of tumor cells to the cytocidal activity of TNF. It is also known that IFNs have a potentiation effect on the cytocidal activity of TNF, similar to the effect of a sensitizing agent.

It was also recently revealed that TNF, which was believed to have a selective antitumor function, may also mediate destructive effects on normal tissues. Thus TNF, with or without a sensitizing agent or another potentiating material, while being potentially effective as a therapeutic material against tumor cells, may also be potentially deleterious to normal cells.

It has previously been shown (50) that treating cells with crude leukocyte-produced cytokine preparations can result in decreased vulnerability to the cytotoxic effect which the cytotoxins (TNF and the related protein-lymphotoxin) in such preparations can exert. That protective effect was observed when applying preparations of the cytotoxins for a few hours and then applying them again in the presence of cycloheximide (CHI). The extent of cell death in case of treatment with the leukocyte-produced cytokine preparations prior to the treatment with the same preparations in the presence of CHI, was much lower than that observed in applying these preparations right away in the presence of CHI. The active ingredient in the leukocyte-produced cytokine preparations was not known.

The identification, in accordance with the present invention, of IL-1 as the leukocyte-produced cytokine desensitizing cells to the cytotoxic effect of TNF (i.e. decreasing the responsiveness to the destructive effect of TNF) and the studies which followed on both in vitro and in vivo systems have enabled to attain the present invention.

SUMMARY OF THE INVENTION

The invention provides methods for modulating the effects of TNF and IL-1, both the deleterious and the therapeutical effect of these cytokines. In case of deleterious effects, the invention provides methods for modulating the lethality of TNF and/or IL-1 in mammals, by administering to a mammal sub-deleterious amounts of TNF and/or IL-1. The TNF and/or IL-1 to be modulated may be endogenous, i.e. generated in the organism in severe cases in amounts deleterious to the organism, or exogenously administered to a patient in amounts which are potentially deleterious.

The TNF and IL-1 used in the compositions and in the method of the invention may be of any origin, native or recombinant. All types of TNF are contemplated by the invention, in particular TNF itself also called TNF-alpha, and TNF-beta, also called lymphotoxin. In the case of IL-1, all subtypes are considered, in particular, IL-1-alpha and IL-1-beta.

Also within the scope of this invention is the use of TNF- and IL-1-like peptides in the method and compositions of the invention. These are polypeptides displaying an immunological or biological activity of human TNF or IL-1.

Also contemplated for use in the invention are derivatives of TNF and IL-1 and of TNF- and IL-1-like peptides, including salts of either or both the carboxyl and the amino terminal or side chain groups and covalent modifications of the polypeptide terminal residues or side chains. Accordingly, the terms TNF and IL-1 are intended to include all of the above-mentioned forms.

It may be desired to potentiate the therapeutical effect of TNF in very severe cases by administering it together with IL-1 and vice-versa. To this end there are provided by the invention, for the first time, compositions comprising TNF and IL-1 (or a derivative or TNF -or IL-1-like peptide) and at least one pharmaceutically acceptable excipient. These compositions may be useful in critical cases, provided their deleterious effect can be overcome.

When therapeutically effective but potentially deleterious amounts of TNF or IL-1 are administered to a patient, the preferred method of the invention comprises administering the sub-deleterious amounts of TNF or IL-1 prior to the administration of the therapeutically effective but potentially deleterious amounts of TNF or IL-1. Either TNF or IL-1 can be administered as a single active material; however a combination of the two materials can also be used for administration both at the pretreatment stage of administration of sub-deleterious amounts and at the second stage of administration of the therapeutically effective amounts.

In accordance with the invention the TNF and/or IL-1 may be administered without any additional active material, but in accordance with a preferred embodiment of the invention the therapeutically effective but potentially deleterious amounts of TNF and/or IL-1 are administered in combination with effective amounts of a sensitizing agent. Preferred sensitizing agents are metabolic blockers or chemotherapeutically active drugs, such as Actinomycin-D or D-galactosamine. The sensitization can also be effected by ionizing irradiation treatment.

In accordance with yet another preferred embodiment of the invention, the method for modulating the deleterious effects of the TNF and/or IL-1 involves administration of IFNs at different stages of the treatment, either prior, following or simultaneously with the administration of the non-deleterious amount of IL-1 and/or TNF. Interferons of any origin, native or recombinant, and of all types and subtypes—alpha, beta or gamma, may be used in the methods and compositions of the invention. In a preferred embodiment, recombinant IFN-gamma is used.

The invention also provides for a method for modulating the deleterious effects of TNF and/or IL-1 wherein the TNF and/or the IL-1 and optionally the sensitizing agent or the interferon are targeted to a specific cell. Targeting is carried out by an antibodt recognizing specific cell surface antigen, or by other known methods based on cell specific characteristics, such as association with hormone acting on such cells.

The invention further provides a method for monitoring the modulation of the TNF effect in a patient treated with sub-deleterious amounts of IL-1, comprising the quantitation of TNF receptor level in cell samples of said patient. Preferred cell samples are peripheral blood leukocytes. This aspect of the invention is based on the finding by Applicants that binding of radiolabeled TNF to cell surface receptors was markedly reduced subsequent to the treatment with IL-1. The decrease in TNF binding was initiated within minutes of application of IL-1 and was not due to competition of IL-1 and TNF for binding to a common receptor, but rather reflected reduced expression of the receptor for TNF as part of the cellular response to IL-1. The regulation is reversible and the TNF receptor level is fully recovered within a few hours of removal of IL-1 (see table III).

In accordance with another aspect of the invention, there are provided compositions comprising effective amounts of TNF and IL-1 with at least one pharmaceutically acceptable carrier. The compositions of the invention can be prepared by pre-mixing the active ingredient or by tandem administration of each of the active ingredient, i.e. by in vivo mixing. The nature of the carrier depends on the way it is applied for therapeutic purposes—be it in the form of a cream or lotion—for topical application or in the form of liquid, in which the active materials will be stabilized by adding components such as human serum albumin, for injection application. The TNF, for example, is effectively cytotoxic to tumor and to virus infected cells at concentrations as low as 10 picograms/ml. The amounts of TNF and/or IL-1 applied for therapy will be adjusted to reach such range of concentrations, or higher ones, in the target tissues. The compositions may also comprise sensitizing agents, e.g. metabolic blockers such as cycloheximide (CHI), Actinomycin D or Mitomycin C D-galactosamine, or interferons, particularly IFN-gamma.

DESCRIPTION OF THE DRAWINGS

The present invention is further described, by way of example, with reference to the accompanying drawings, in which.

DETAILED DESCRIPTION OF THE INVENTION

Figure 1A:
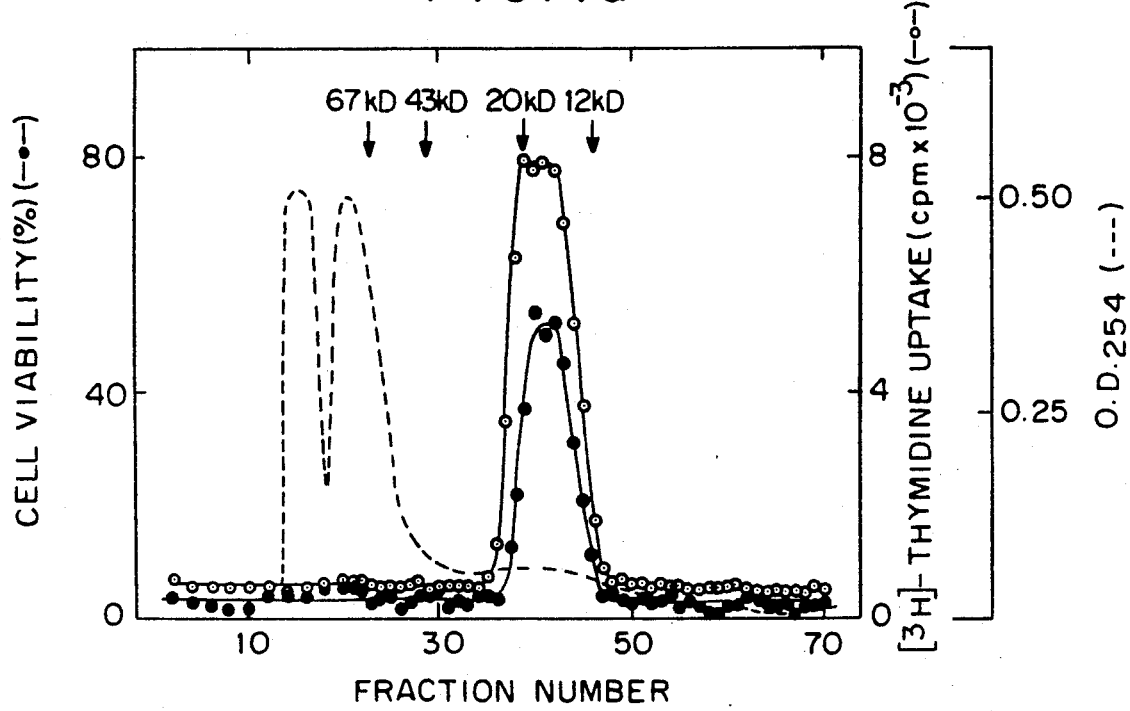
FIGS. 1a, and 1b show the identification of IL-1 as the leukocyte-produced cytokine which desensitizes cells to the cytotoxicity of TNF. A crude cytokine preparation produced by activated U937 cells was subjected to fractionation in two stages: (a) by gel filtration on Ultrogel AcA 54 column in 1M NaCl, 10 mM sodium phosphate buffer, pH 7.4, 0.1 mM EDTA, 0.1% polyethylene glycol, 30% ethylene glycol and (b) by ion exchange HPLC or Mono Q column. The sample was applied in 20 mM triethanolamine, pH 10, and eluted with a gradient of NaCl (0–0.125 M). At both stages the desensitization activity and IL-1 activity (Thymidine uptake by thymocytes) copurify. By analysis with sodium dodecyl sulfate polyacrylamide gel electrophoresis, it was found to contain a major protein with approximate m.w. 17,000 and only minor amounts of other proteins of lower m.w.
Figure 1B:
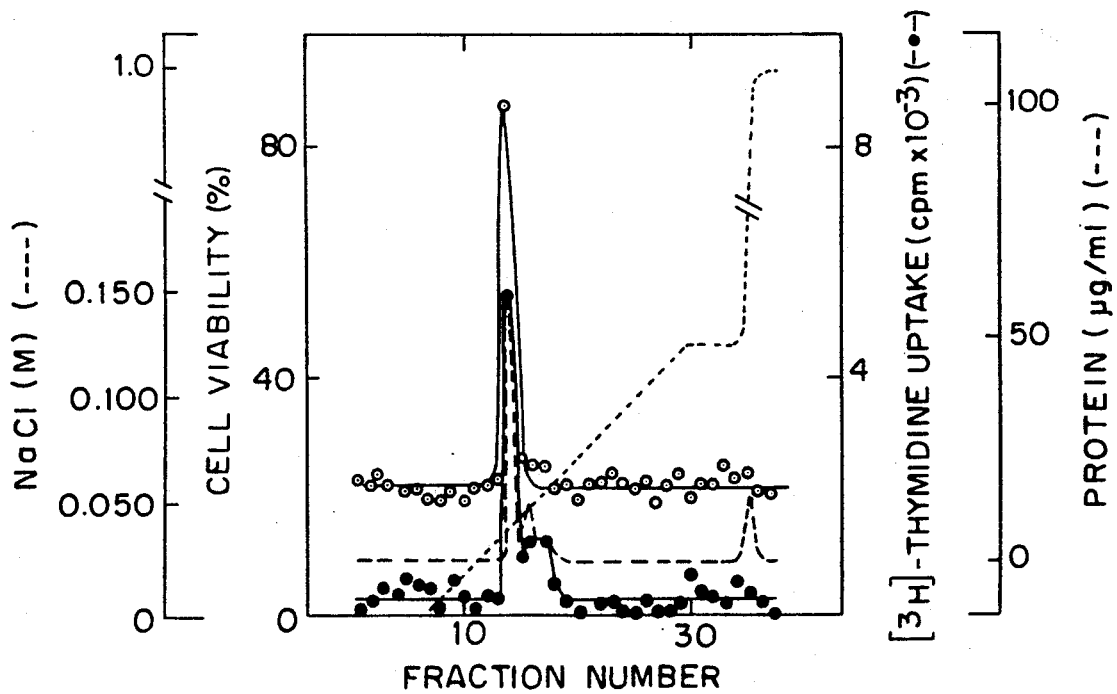

1. Identification of IL-1 as the leukocyte produced cytokine desensitizing cells to the cytotoxic effect of TNF Crude preparations of leukocyte-produced cytokines were exposed to pH 2.0. TNF is inactived by such treatment—both with regard to its cytolytic function and to its ability to induce resistance to its own cytotoxicity. The TNF-free preparations were fractionated as shown in FIGS. 1a and 1b and the desensitization activity copurified with IL-1. Desensitization activity was measured by applying the tested sample on human SV80 cells for a few hours and subsequently applying TNF and CHI and measuring the extent of resulting cell death.

Figure 2:
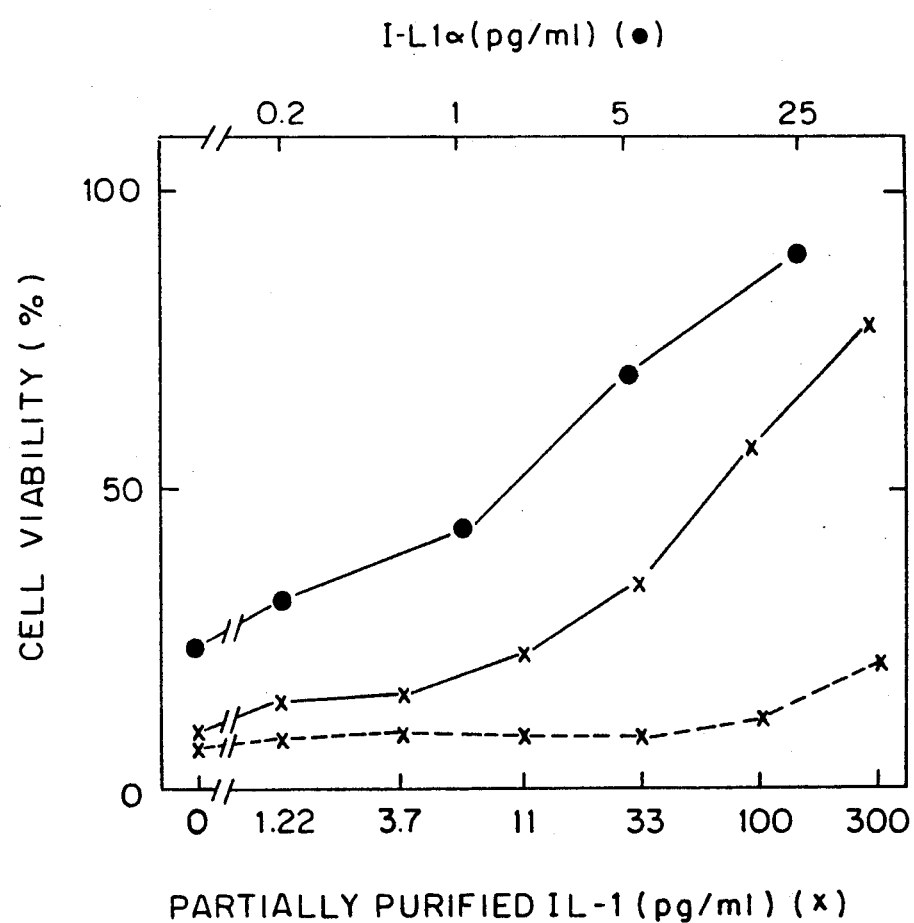
FIG. 2 shows the identification of IL-1 as a leukocyte-produced cytokine which desensitizes cells to the cytotoxicity of TNF by studying the protective activity of IL-1 and neutralization of the protective activity of pH 2.0-treated cytokines with antiserum to Il-1. Concentration dependence of the protective effect of IL-1 (●) and of a preparation of pH 2.0-treated cytokines, subjected to purification following the step of gel filtration FIG. 1a, after incubation for 2 h at 4° C. with medium containing monospecific rabbit antiserum against IL-1 (applied at a dilution of 1:100) (x---x), or with medium alone (x-x).

Further confirmation of the identity of the desensitizing cytokine as IL-1 was demonstrated by the neutralization of IL-1 with a monospecific antibody against IL-1, as shown in FIG. 2. Titration of the desensitization activity of semi-crude cytokine preparation produced by the U937 cells with (x---x) or without (x-x) treatment of this preparation with antiserum raised against IL-1, demonstrated that IL-1 can mediate the desensitizing effect (●).

Figure 3A:
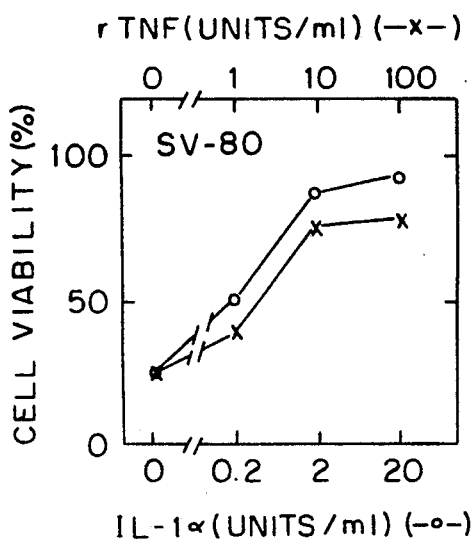
FIGS. 3a-3d are a comparison of the protective activity of rTNF and IL-1 in the human SV-80, HeLa and L132 and mouse L929 cell lines. The protective effect was elicited by incubation for 4 hours with the indicated concentrations of the two cytokines, followed by 12 hours incubation with rTNF (100 U/ml)+CHI (50 μg/ml).
Figure 3B:
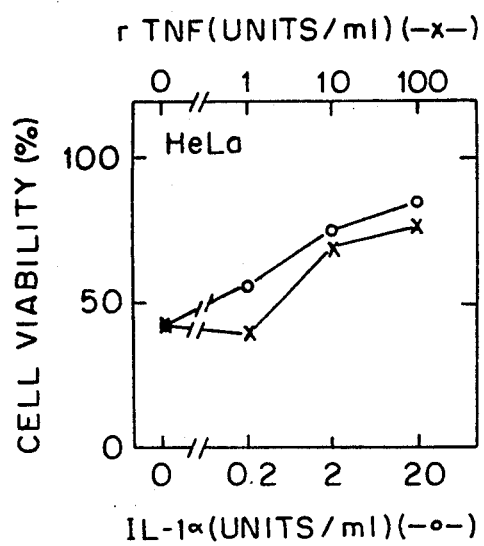
Figure 3C:
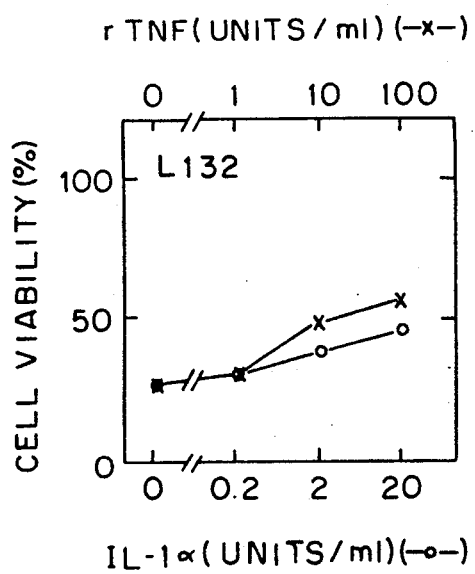
Figure 3D:
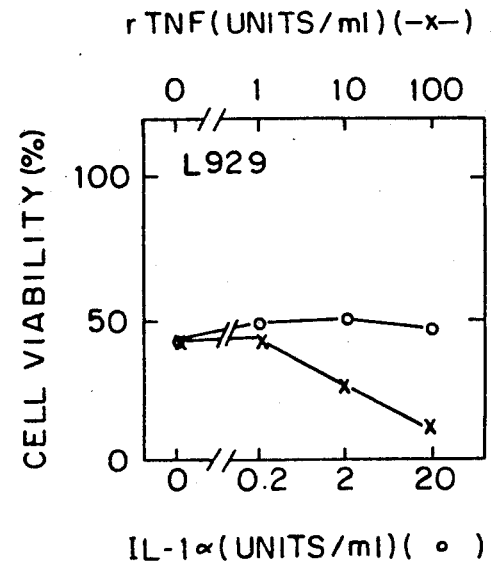

Desensitizing effect of IL-1 in cells of three different human cell lines: SV80, HELA, L132 was also demonstrated, illustrating the generality of this phenomenon, as shown in FIGS. 3a-3c.

Cytolytic and protective (desensitization) activities of the cytokines were determined in all the figures using SV-80 cells which, for measurement of cytolytic activity, were incubated with serial dilutions of the tested cytokine for 12 hours together with 50 μg/ml CHI; for measuring protective activity, they were incubated for 4 hours with the tested cytokine and then for 12 hours with TNF, at the indicated concentrations, together with 50 μg/ml CHI. The extent of cell killing was quantitated by the neutral-red uptake assay. A unit of cytolytic activity is defined as the concentration of the tested cytokine at which the amount of cells remaining viable was 50% of those that remained viable on incubation with CHI alone. A unit of protective activity is defined as that cytokine concentration protecting 50% of the cells from killing by TNF.

Thus, the component of pH 2.0-treated cytokine preparations inducing resistance to killing by TNF was identified as IL-1, based on the following findings:

a) The protective activity and a typical activity of IL-1 (thymocyte activation) copurified, when crude preparations of U937-produced cytokines were subjected to a series of fractionation steps, resulting in effective purification of IL-1 (See FIGS. 1a and 1b).

b) Monospecific antiserum to IL-1 neutralized the protective activity of such preparations (See FIG. 2). c) IL-1 of different souces induced resistance to the cytotoxicity of TNF as effectively as did the crude preparations of cytokines; some resistance was observed even on treatment with as little as 0.1 unit (3 pg) of IL-1 per ml, as shown in FIG. 2. Bacterial lipopolysaccharide, which may contaminate preparations of IL-1, did not induce resistance even when applied at concentrations as high as 10 μg/ml.

2. Preparation of native purified IL-1

Native purified IL-1 was prepared as follows: Crude preparations of cytokines induced in the human histiocytic lymphoma cell line U937 (47) by 4-beta-phorbol-12-myristate-13-acetate (5 ng/ml) and Sendai virus (48) were adsorbed to controlled-pore glass beads (PG-350-200, Sigma, St. Louis, Mo). Most of the protective activity and of LAF activity, and only a minor part of the cytolytic activity and of IFN was recovered in the unbound material. It was concentrated by ultrafiltration on an Amicon YM5 membrane and depleted of IFN-alpha and of all residual TNF by application on immunosorbent columns constructed of monoclonal antibodies against them. It was then dialyzed for 12 h against phosphate buffered saline, pH 2.0. Insoluble material was removed by centrifugation. Following equilibration with 1M NaCl, 10 mM sodium phosphate buffer, pH 7.4, the protein was fractionated on an Ultrogel AcA 54 column (16×110 mm) in 1M NaCl, 10 mM sodium phosphate buffer, pH 7.4, 0.1 mM ethylene diamine tetraacetic acid, 0.1% polyethylene glycol ($M_r$ 7000–9000) and 30% ethylene glycol. Fractions of 2.5 ml were collected and assayed for LAF activity and for induction of resistance to TNF. The active fractions were pooled, concentrated, equilibrated with 20 mM sodium phosphate, pH 7.4, and applied to a DEAE Sephacel column (7 ml) (Pharmacia, Uppsala, Sweden) preequilibrated with the same buffer (49). Both the protective and the LAF activity were fully recovered in the material which remained unbound to the column. In analysis by sodium dodecyl sulfate polyacrylamide gel electrophoresis, that material was found to contain a major protein with an $M_r$ of about 17000 and only minor amounts of other proteins of lower $M_r$. (LAF activity-Lymphocyte activating factor activity).

3. Interrelations between the effects of IL-1 and TNF on cell viability

Figure 7:
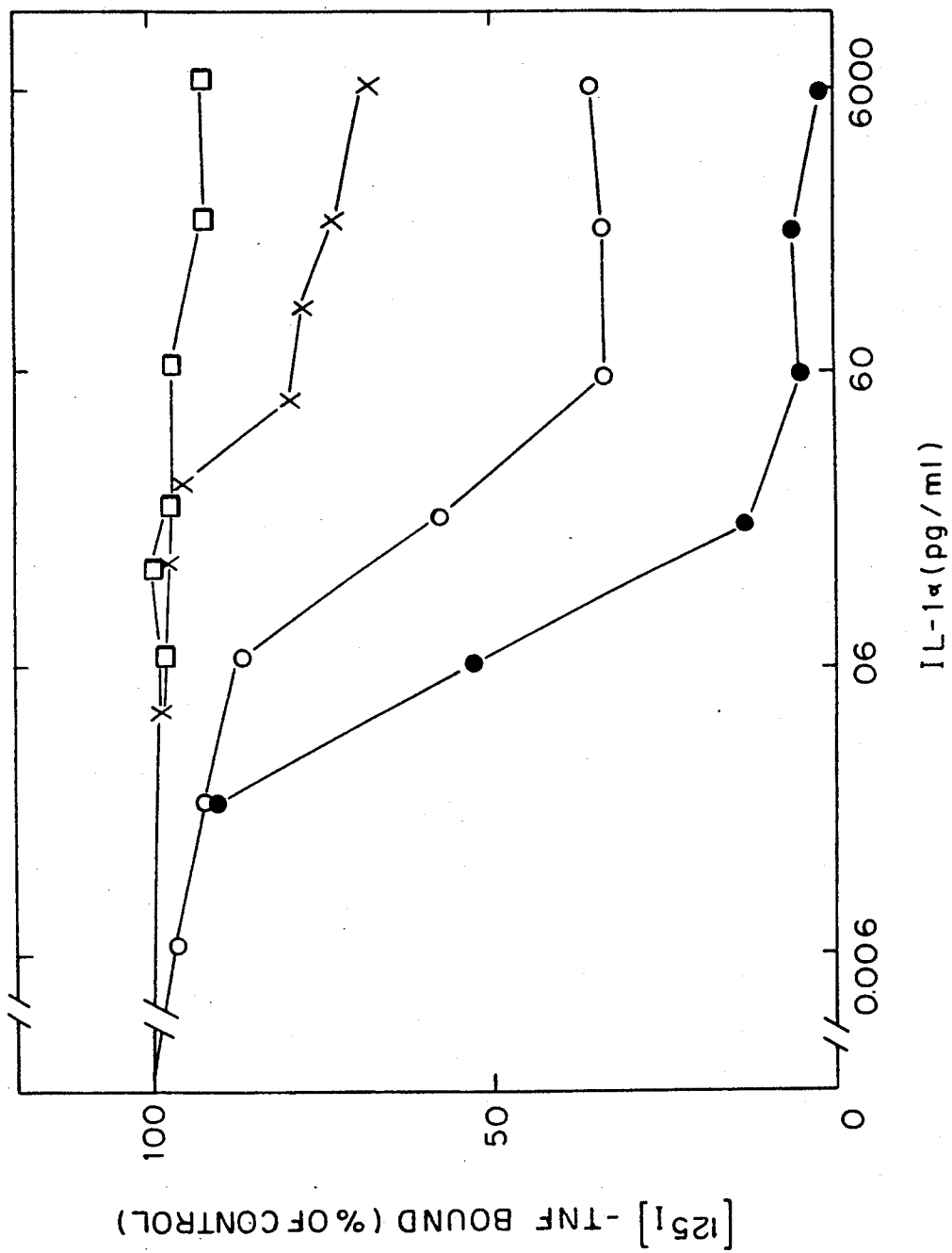
FIG. 7 is the dose response curve of IL-1 induced reduction in TNF binding to various cells. FS11 foreskin cells (●), SV80 cells (○), HeLa cells (x) and U937 cells (□) were incubated for 4 h with the indicated concentrations of IL-1 and the specific binding of $^{125}$I-INF, applied at 3.6 ng/ml was then quantitated as described for Table I, and is presented as percentage of the binding to untreated control cells (1800 CPM in FS11 cells, 1400 CPM in SV80 cells, 5500 CPM in HeLa cells and 3300 CPM in the U937 cells).
Figure 9A:
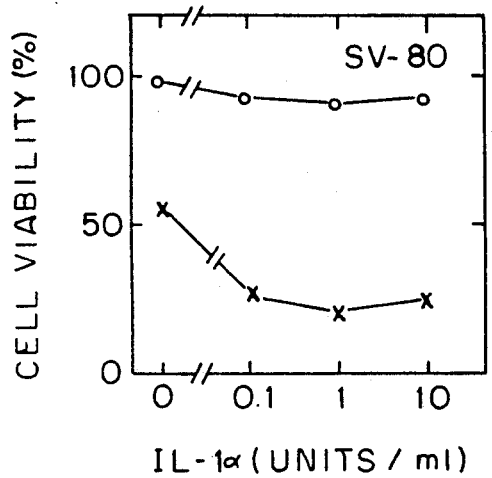
FIGS. 9a-9b show the potentiation of the cytotoxicity of TNF by IL-1 in the presence of the metabolic blocker cyloheximide (CHI). The cytolytic effect was studied on four different cell lines, SV-80, HeLa, L132 and L929. IL-1 was applied for 12 hours at the indicated concentrations either together with CHI (50 μg/ml) (○) or with both CHI (50 μg/ml) and rTNF (10 U/ml) (x).
Figure 9B:
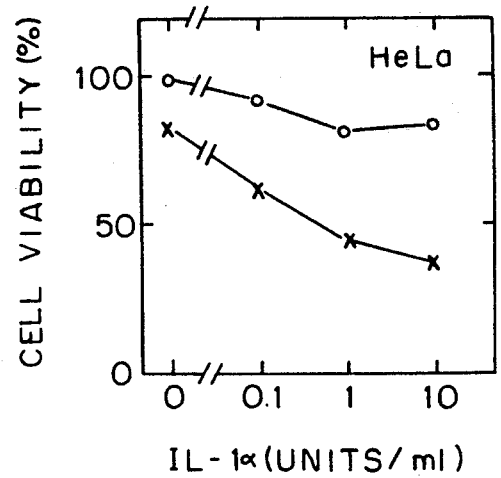
Figure 9C:
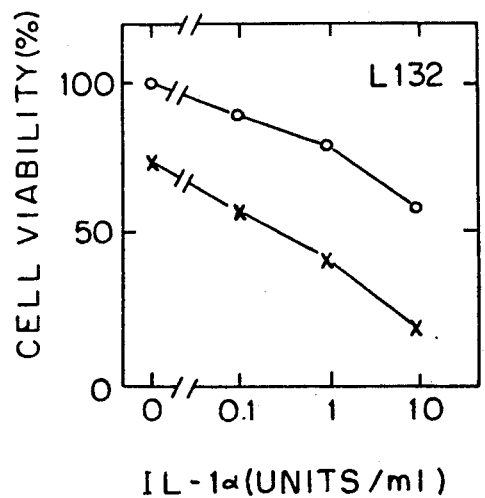
Figure 9D:
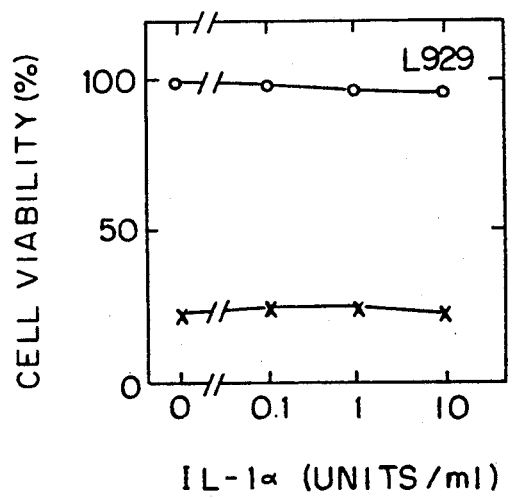

The protective effect of IL-1, induced in human SV-80 cells in the absence of CHI, was comparable to that induced by TNF, as shown in FIG. 3a. However, as shown in FIG. 9a, unlike TNF, IL-1 has just a barely detectable cytolytic effect on these cells in the presence of CHI. As illustrated in FIG. 9a under particular situations, i.e. when protein synthesis in the cell is blocked, IL-1 can have the reverse-potentiation effect on cell killing. At even minute concentrations, IL-1 potentiated the cytotoxicity of TNF, increasing the effectivity of cell killing by low concentrations of TNF to that elicited by as much as 25-fold higher concentrations in the absence of IL-1. In two other human cell lines, HeLa and L132, IL-1 by itself was clearly cytolytic when applied together with CHI, and this cytotoxicity appeared to be additive to that of TNF (FIG. 7). Both in HeLa and in L132 cells, a protective effect of IL-1, as well as of TNF, could be observed when these cytokines were applied in the absence of CHI. (FIGS. 3b and 3c).

IL-1 or TNF provide protection not only against the cytotoxicity mediated in the presence of CHI, but also against killing of cells in which synthesis of proteins has been suppressed by other agents. Table II shows the cytotoxicity of TNF against SV-80 cells in the presence of the protein synthesis inhibitor, emetine and the RNA synthesis inhibitor, actinomycin D. Like CHI, these two other inhibitors sensitized the SV-80 cells to killing by TNF; and as with CHI the sensitization by both inhibitors is greatly reduced by pretreatment either with IL-1 or with TNF in the absence of the inhibitors.

4. Relation of the decrease in TNF receptors to increase in resistance against the cytotoxicity of TNF observed following treatment with IL-1.

Figure 4:
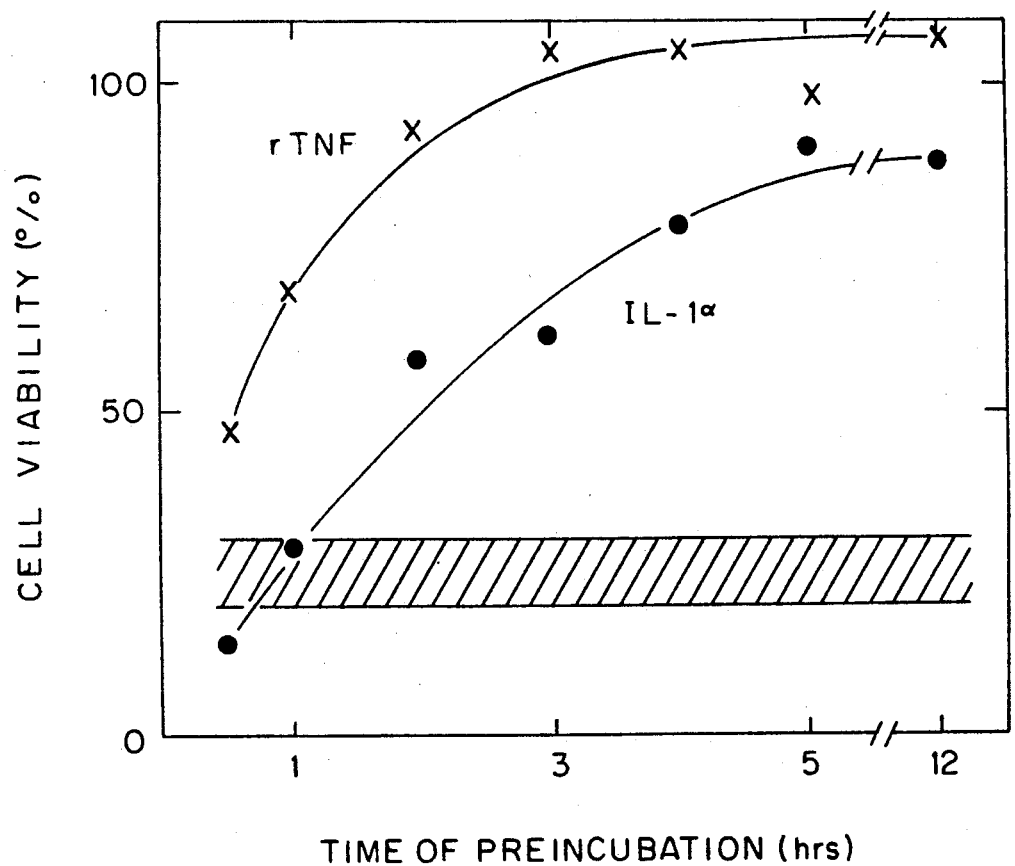
FIG. 4 shows the kinetics of induction of resistance to the cytotoxicity of TNF and by IL-1. SV-80 cells were preincubated for the indicated time periods with rTNF (20 pM) (x) or IL-1 (7 pM) (●) (broken line: viability in cultures preincubated with growth medium alone). Thereafter the cells were rinsed and incubated with TNF (100 pM)+CHI (50 μg/ml) for 12 hours. Cell viability is expressed in percentage of viability compared with cultures challenged with CHI alone.
Figure 5:
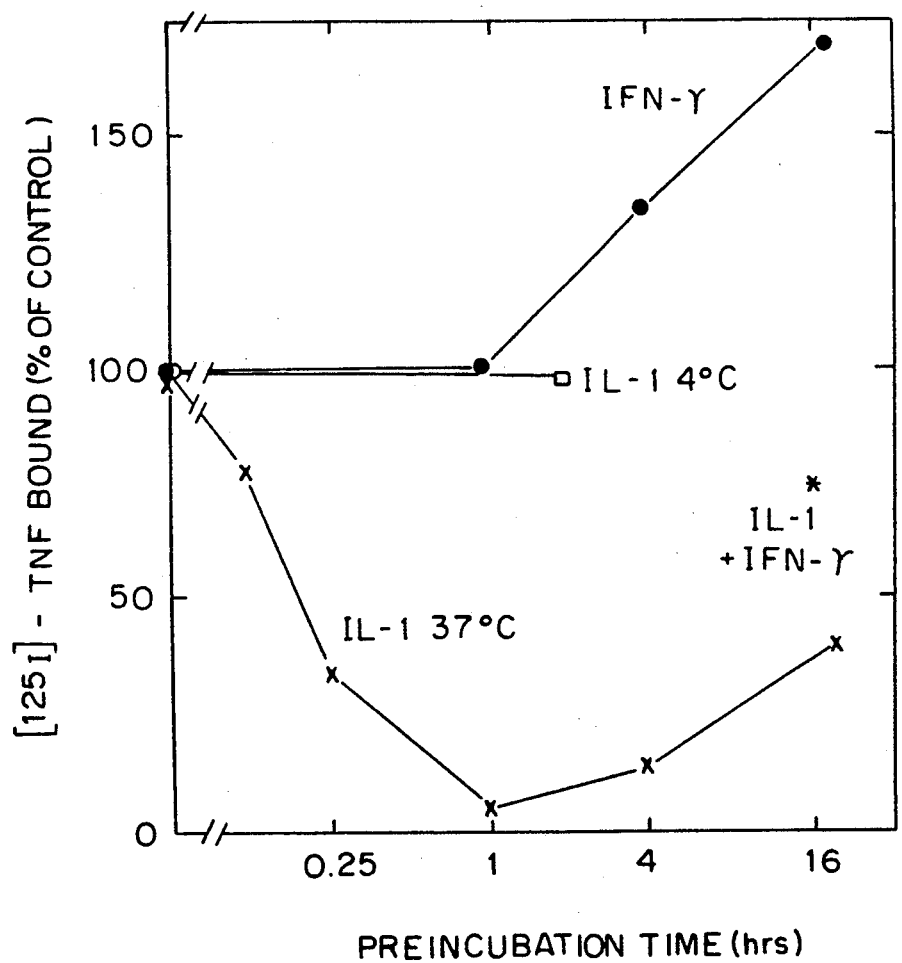
FIG. 5 shows the kinetics of the decrease in binding of TNF to SV-80 cells in response to IL-1 and the increase in binding in response to IFN-gamma. IL-1 (3.5 pM) was applied on SV-80 cells either at 4° C. (□) or at 37° C. (x) and rIFN-gamma (0.6 nM) at 37° C. (●). Following incubation for the indicated times specific binding of $^{125}$I-TNF (applied at 0.9 nM) was quantitated. Results are expressed as percentage of the binding to untreated cells (4286 cpm). The binding of $^{125}$I-TNF following incubation for 16 h with rIFN-gamma (0.6 nM) and then for a further 4 h with IL-1 (3.5 pM) is also shown (*).

Cells treated with IL-1 as well as with TNF become more resistant to the cytolytic effect of TNF (50). As shown in FIG. 4, the induction of resistance by IL-1 and by TNF followed a similar time course, save that with TNF resistance was reached earlier. Resistance to cytolysis kept increasing until about 5 h following application of IL-1 (FIG. 4), even though the TNF receptor level had reached its lowest value already at about 1 h (FIG. 5). This slow development of resistance in treating SV-80 cells with IL-1 can perhaps be related to the fact that in these cells IL-1 can also have the opposite effect. While inducing resistance to cytolysis when applied prior to the application of TNF. it is found to potentiate cytotoxicity when applied together with TNF (48). Indeed, as shown in FIG. 4, SV-80 cells treated with IL-1 for less than an hour exhibited a higher vulnerability to the cytolytic effect of TNF did the untreated cells (dashed line in FIG. 4).

Figure 8:
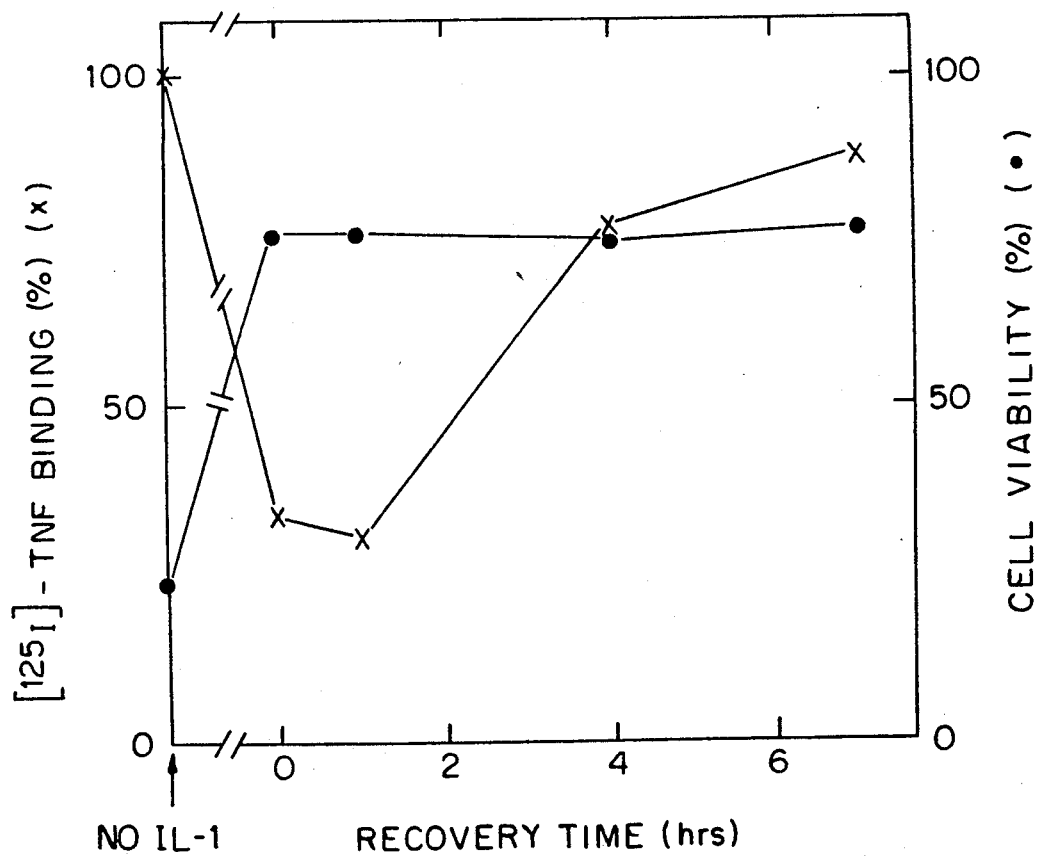
FIG. 8 shows the binding of TNF and the sensitivity to its cytolytic effect following removal of IL-1 from pretreated cells. SV-80 cells were incubated for 4 h with IL-1 (3.5 pM), rinsed thrice and tested at various times thereafter for binding of TNF (x) and for sensitivity to its cytolytic effect (●). Binding of radiolabelled TNF (0.2 nM) is presented in percent of binding to cells which had not been treated with IL-1 (2595 cpm); the extent of killing by TNF (100 pM) is presented as percent viability compared to cultures challenged with CHI alone.

An even more pronounced discrepancy between the effect of IL-1 on the receptors for TNF and on cell vulnerability to cytolysis by TNF could be observed in the recovery from those two IL-1 effects. As shown in FIG. 8, removal of IL-1 from SV-80 cells was followed by a quite rapid recovery of the receptors for TNF, but not of the vulnerability to its cytolytic effect. At 7 h following removal of IL-1, TNF receptors were restored almost to their normal level while the resistance to killing by TNF remained unaltered. The maintenance of resistance to killing by the protein following removal of IL-1 from treated cells and the recovery of TNF receptors indicates that IL-1 induces some other changes which contribute to cell resistance to killing by TNF, in addition to its effect on the receptors to TNF.

5. Decrease of TNF receptors in response to IL-1

Figure 6:
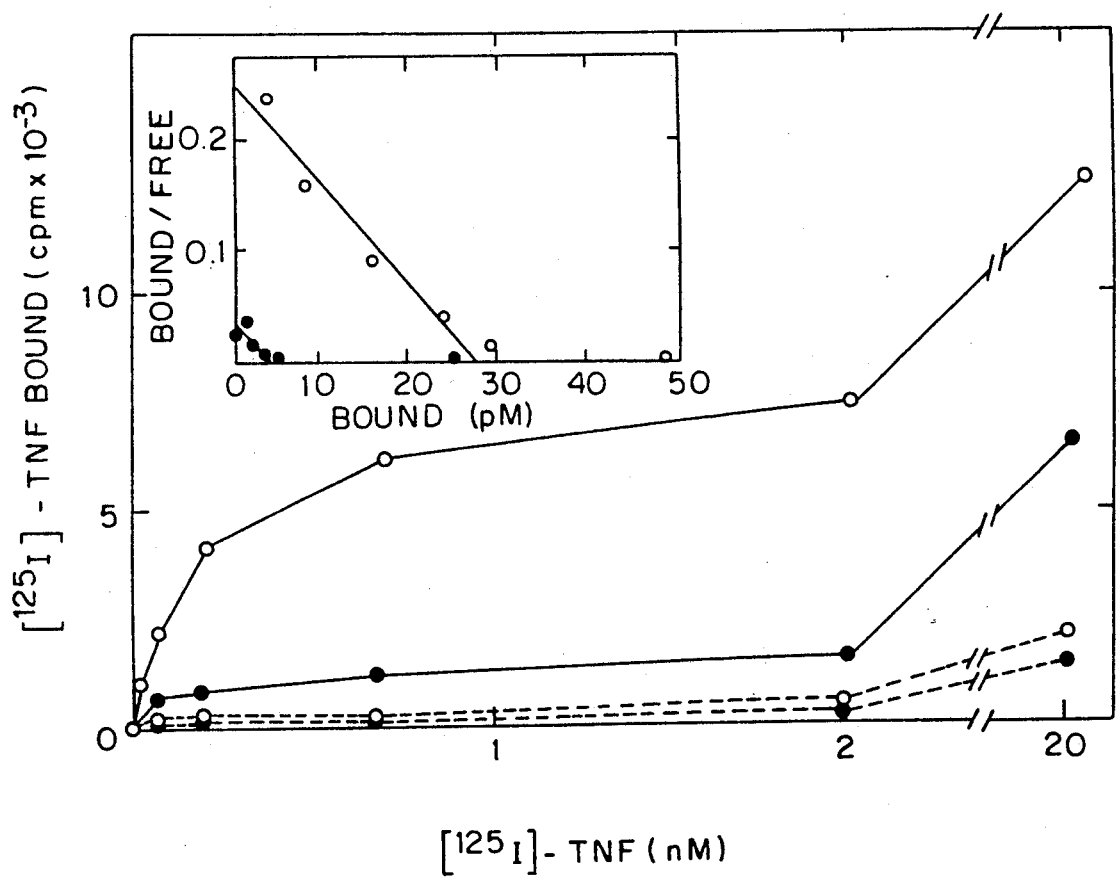
FIG. 6 shows the binding of the radiolabelled TNF to IL-1 treated and non-treated SV80 cells. Radiolabelled TNF was applied, at the indicated concentrations, either in absence (solid line) or presence (broken line) of 1000-fold excess unlabelled TNF to cells treated for 4 h with IL-1 (60 pg/ml) (●) or to untreated cells (○). Scatchard plot analysis of the binding using the LIGAND program[25] is shown in the inset.

Treatment of SV-80 cells with IL-1 resulted in decreased expression of the receptors for TNF. In kinetic studies, TNF binding was found to decrease within a few minutes of IL-1 application, reaching its lowest level at about 1 h. Thereafter, it increased slightly; nevertheless even after 20 h in the presence of IL-1, TNF binding was significantly lower than in untreated cells (FIG. 5). Scatchard plot analysis of the binding shown in FIG. 6, indicated that in both IL-1 treated and untreated cells, TNF binds to receptors of a homogeneous nature and that the affinity of the binding sites remains unaltered following IL-1 treatment, while their density greatly decreases (900 receptors/cell and Kd of $9.7 \times 10^{-11}$M in cells treated for 4 h with 60 pg/ml of IL-1, as compared to control values of 6200 receptors/cell and Kd of $1.1 \times 10^{-10}$M). In repeated examinations, variations in the level of receptors for TNF (2234 to 6960 binding sites/cell) and some variation also in the estimated values of Kd ($9.6 \times 10^{-11}$M to $3.1 \times 10^{-10}$M) were observed. Yet in all experiments IL-1, as well as PMA, were found to affect only the number of binding sites for TNF and not their affinity. Data from a representative example are shown in FIG. 6. (PMA-4-beta-phorbol-12-myristate-13-acetate).

The decrease in TNF receptors was temperature dependent. As shown in FIG. 5, it could not be observed at 4° C., even when IL-1 was added a few hours prior to the addition of TNF or at a great excess (as much as 500-fold) of TNF. On the other hand, it appears that the effect of IL-1 was not dependent on protein synthesis.

TNF and IL-1 were found not to compete directly for binding to their target cells. These findings indicate that the receptors to TNF and IL-1 are distinct molecules and that the expression of the receptors to TNF can be subject to regulation by IL-1. As shown in Table I and FIG. 5, at 4° C. IL-1, added to cells either together with radiolabelled TNF or a few hours prior to application of TNF, had no effect on binding of TNF. In contrast, at 37° C., treatment of the human fibroblastoid SV80 cells and of foreskin fibroblasts (FS-11) with IL-1 resulted in a marked and rapid reduction of TNF binding. Binding was maximally inhibited at 1 h following application of IL-1 and then slowly recovered. However, even 20 h following initiation of IL-1 treatment the binding was still markedly reduced.

The effect of IFN-gamma on TNF receptors was also examined as shown in FIG. 5. As in other cells, IFN-gamma induced in the SV-80 cells an increase in receptors for TNF which was initiated a few hours following the addition of IFN. Cells in which the receptors for TNF had been increased by IFN also responded to IL-1 by a decrease in the number of TNF receptors, although not to the same low level as in cells which were not treated with IFN. Quantitation of IFN-gamma receptors in the SV-80 cells showed no alteration in their level after treatment of the cells by IL-1 or TNF.

As shown in FIG. 7, human foreskin fibroblasts were found to respond to the effect of IL-1 on TNF binding to an even greater extent than did SV-80 cells. TNF receptors showed a more pronounced decrease and the effect could be observed at lower IL-1 concentrations. Some decrease was induced in these cells by as little as $3.5 \times 10^{-14}$M IL-1 (0.02 LAF U/ml). Decrease of TNF receptors was induced by IL-1 also in HeLa cells although less effectively than in the SV-80 cells. On the other hand, no decrease in TNF receptors could be observed when U937 histiocytic lymphoma cells were treated with IL-1. Examining the binding of radiolabelled IL-1 to these different cell types, as shown in Table I, suggested a correlation between the effect of IL-1 and the level of receptors to this protein. IL-1 binding was highest in the FS11 cells, lower in SV80 cells, even lower in HeLa cells, and below detectable levels in U937 cells. TNF did not compete with the labelled IL-1 for the binding. Furthermore, treating the cells for 4 h with TNF (at 17 ng/ml) did not result in a decrease in their ability to bind IL-1 (Table I). Also the binding of radiolabelled rIFN-gamma to the cells was not significantly changed following treatment by IL-1 or TNF.

6. Desensitization to the lethal effects of TNF and of IL-1

Nine to thirteen weeks old Balb/c mice were used in all experiments. TNF, IL-1, LPS, actinomycin-D (Act-D) and D-galactosamine (GalN) were solubilized in PBS and injected i.p.; each in aliquots of 0.5 ml. For lethality determination TNF, IL-1 or LPS were administered alone or 10 minutes following injection of Act-D or GalN; for desensitization experiments mice were injected with TNF or IL-1 12 h prior to a challenge consisting of the same regimen as the lethality testing. Following treatments the mice were continuously observed for a period of 72 h in order to determine the time of their death. In all cases, mice that survived 72 h appeared completely normal at that time. Furthermore, part of these mice were observed for a week and found to show no sign of deterioration. All experiments were performed in duplicate with qualitatively the same results. Two mice were examined for each experimental point, in each of the experiments. Their actual survival time as well as the average of the survival time of the two mice used for each of the points are presented.

Figure 10:
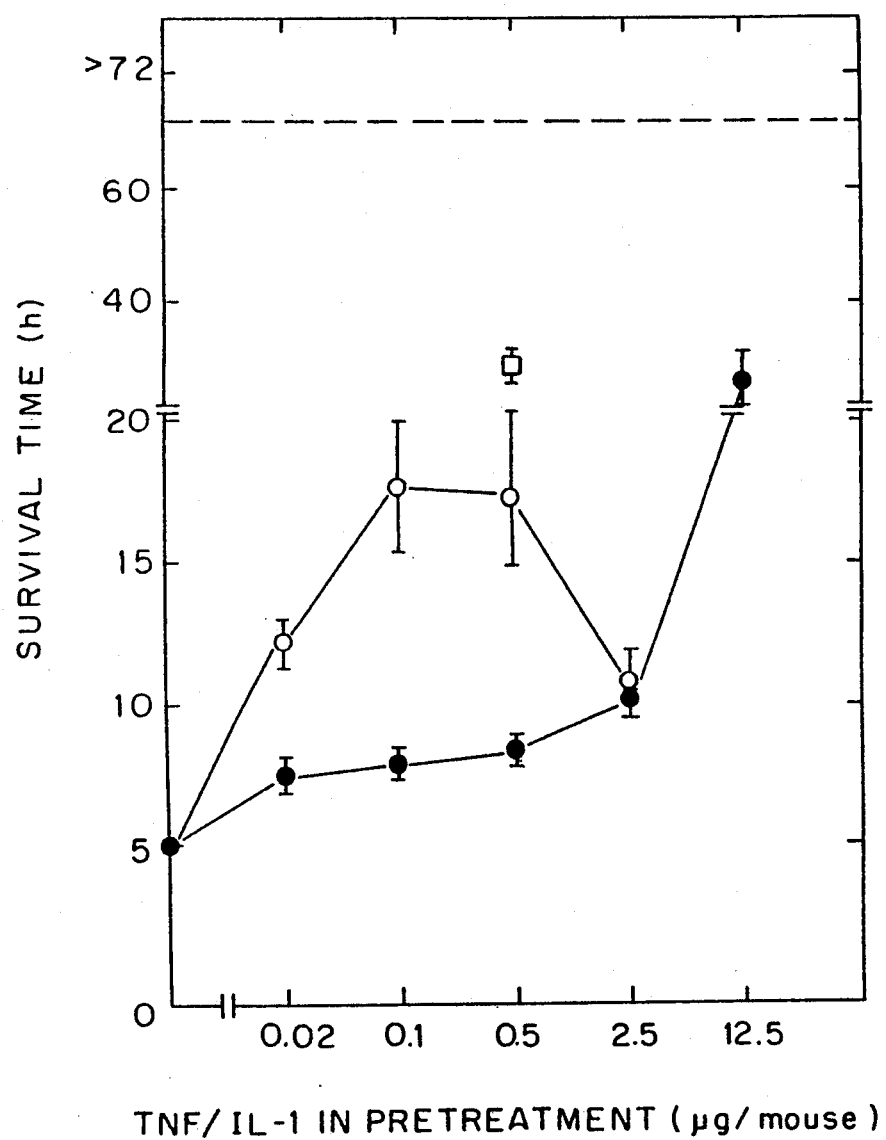
FIG. 10 shows the desensitization effect in mice in response to TNF and to IL-1. Mice were injected with the indicated amounts of TNF (●) or IL-1 (○) or with both TNF and IL-1, each at 0.5 ug/mouse (□). Twelve hours later they were injected again with TNF (5 μg) and Act-D (20 μg) and their survival time thereafter was recorded.
Figure 11:
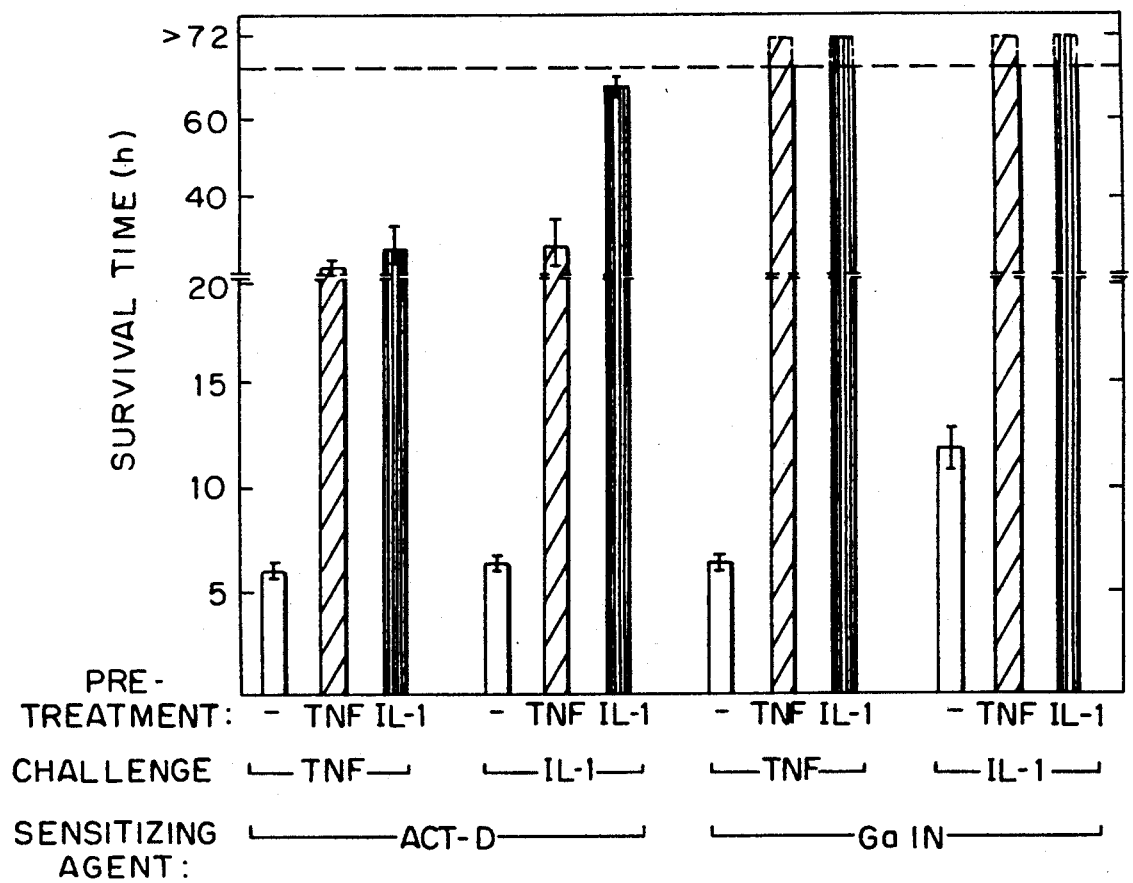
FIG. 11 shows the homologous and heterologous desensitization in response to TNF and to IL-1 in mice. Mice were injected with TNF (5 μg; □) with IL-1 (0.2 μg; Ⅲ) or just with PBS (□). Twelve hours later they were again injected either with TNF (2 μg) or with IL-1 (0.4 μg), this time together with either Act-D (20 μg) or GalN (18 mg) and their survival time thereafter was recorded.

Act-D and GalN sensitize mice to the lethal effect of TNF and IL-1. In an attempt to elucidate the nature of the sensitizing effect of Act-D and of GalN, it was tested whether injection of TNF or IL-1 in the absence of these agents affects the response of mice to a subsequent injection of TNF or IL-1 together with Act-D or GalN. As shown in FIGS. 10 and 11, mice injected with TNF+Act-D 12 h after injection of TNF, survived the lethal effect of TNF+Act-D for a longer time than mice which had not been pre-exposed to TNF alone. That protective effect was prominent in mice which were pretreated with a high dose of TNF (5 μg/mouse) but could clearly be discerned even in mice which were pretreated with as little as 0.02 ug TNF. Similarly, viability of the mice following injection with IL-1+Act-D was prolonged by prior injection with IL-1. Pretreatment with IL-1 also increased the ability of mice to survive a subsequent injection with TNF+Act-D. Inversely, mice pretreated with TNF showed an increased ability to survive the lethal effect of IL-1+Act-D. Injecting mice with TNF and IL-1 together protected them from the lethal effect of TNF+Act-D more effectively than their preinjection either with TNF or IL-1 alone, as exhibited by the rectangular in FIG. 10.

Figure 12:
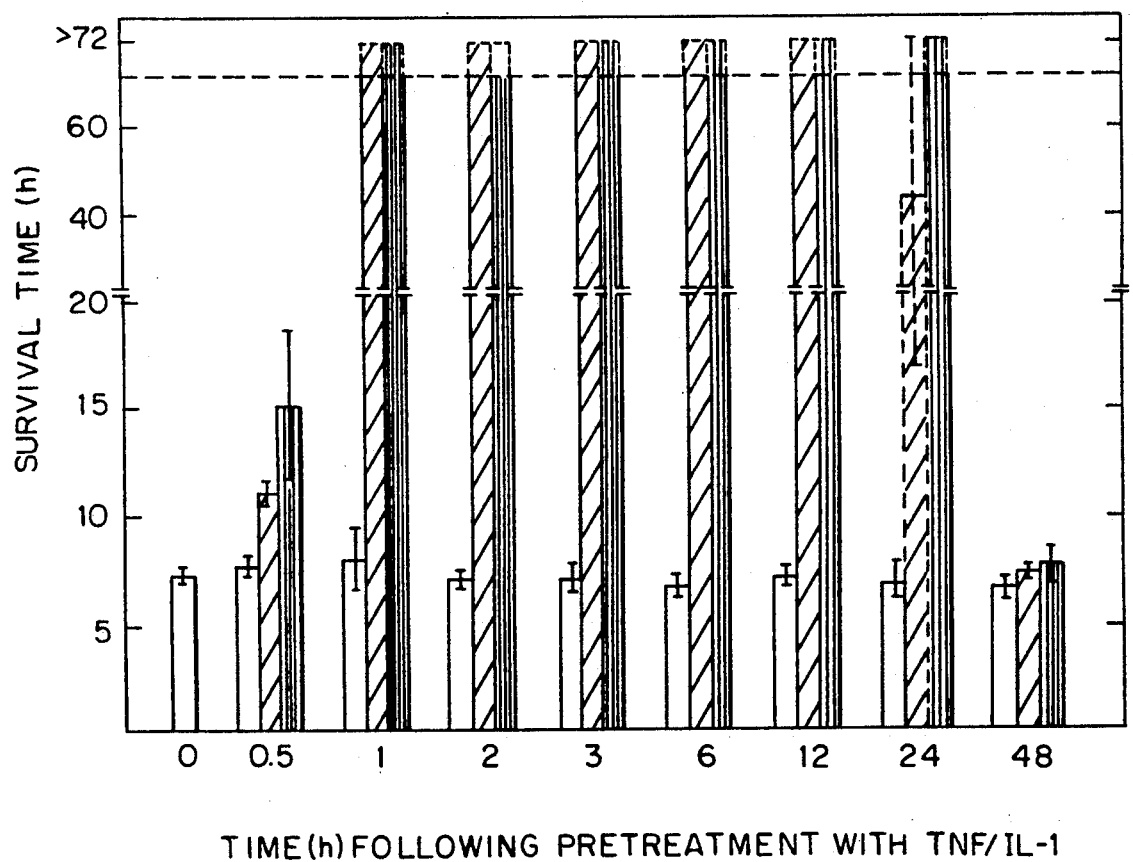
FIG. 12 shows the kinetics of desensitization in response to TNF. Mice were injected with TNF (10 μg; □) with IL-1 (0.4 μg Ⅲ) or just with PBS (□). Following the indicated time they were injected with galactosamine (GalN) (18 mg) and 10' later again with TNF (3 μg) and their survival time thereafter was recorded.
Figure 13:
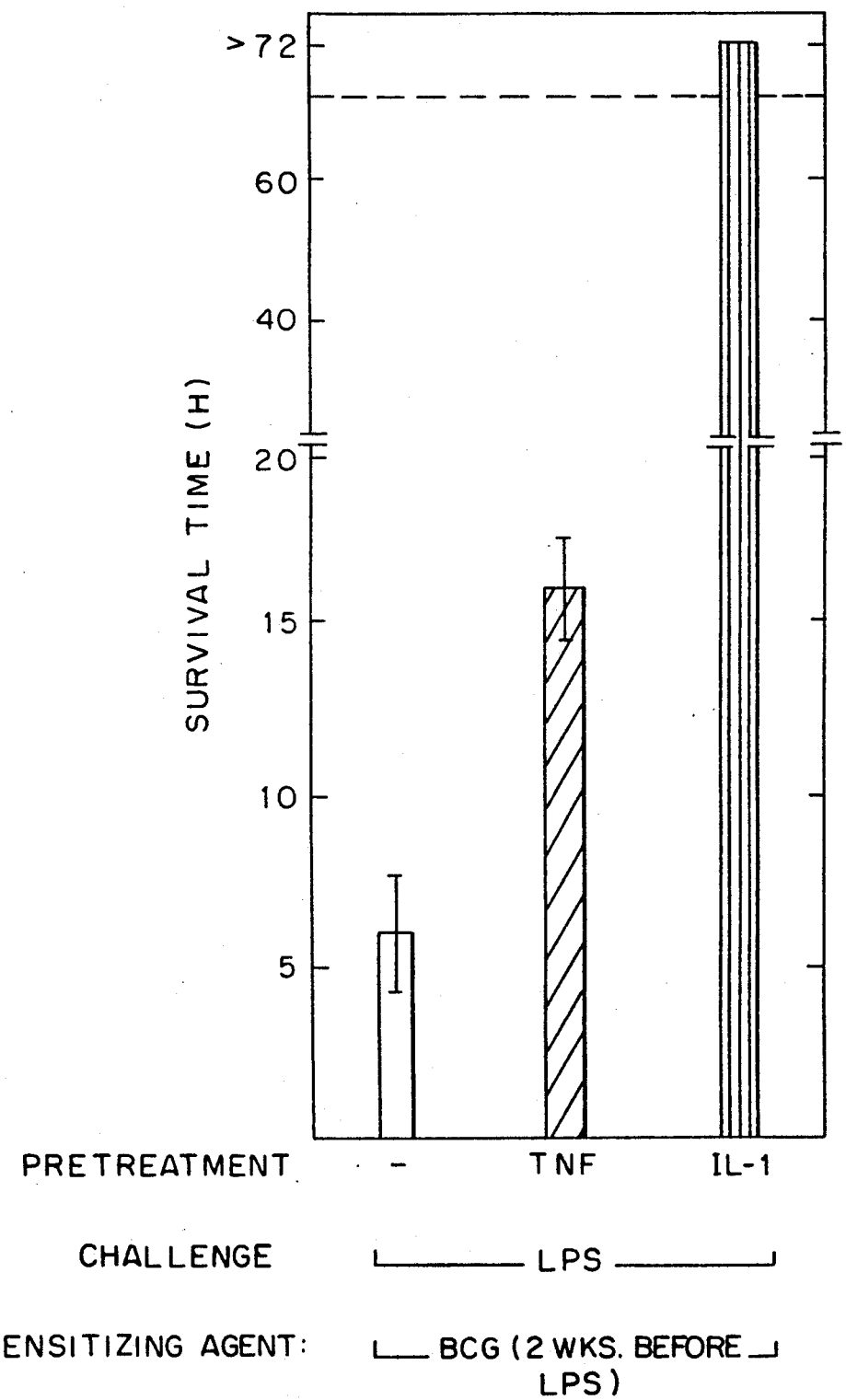
FIG. 13 shows the protective effect of TNF and IL-1, when injected at sublethal doses against lethal effect of bacterial endotoxin (LPS) on BCG primed mice. C57/BL mice were injected intravenously with 0.38 mg Bacillus Calmette Guerin (BCG) in 0.5 ml PBS. Two weeks later they were injected i.p. either with PBS or with TNF (10 μg) or with IL-1 (0.4 μg). Twelve hours later the mice were injected i.v. with 0.5 ml PBS containing LPS (Escherichia coli, serotype 0127:BS8 prepared by phenolic extraction) and their survival thereafter was recorded.

Mice injected with TNF or IL-1 were also protected from the lethal effect of subsequent injection of TNF or IL-1 in the presence of GalN. That protection was even more effective than the protection against the lethal effect which these cytokines exert in the presence of Act-D. At those concentrations of TNF and IL-1 applied in the experiment described in FIG. 11, death in sensitization with Act-D was just delayed by a prior treatment with IL-1 or TNF while death occurring in sensitization with GalN was actually prevented. GalN-sensitized challenges were therefore chosen in examining the kinetics of the protective effect shown in FIG. 12. Partial protection from the lethal effect of TNF GalN, reflected in prolongation of survival time, could be observed already at 30' after injection of TNF or IL-1 alone (10 μg and 0.4 μg/mouse, respectively). One cating to inject the contents of vial A and after a predetermined time interval to inject the contents of vial B.

TABLE I

Effects of IL-1 on the binding of TNF, of TNF on the binding of IL-1, and of TNF and IL-1 on the binding of IFN-gamma to various cells

| | $^{125}$I-TNF | | | $^{125}$I-IL-1 | | | $^{125}$I-IFN-gama | |
|---|---|---|---|---|---|---|---|---|
| | — | competition with IL-1 (30 ng/ml) | pretreatment with IL-1 (60 pg/ml) | — | competition with TNF (17 ng/ml) | pretreatment with TNF (17 ng/ml) | pretreatment with TNF (17 ng/ml) | pretreatment with IL-1 (60 pg/ml) |
| SV80 | 2400 | 2200 | 800 | 400 | 400 | 400 | 1600 | 1600 | 1500 |
| FS11 | 1800 | 1800 | 100 | 900 | 900 | 900 | 1700 | 1800 | 1800 |
| HeLa | 7900 | 7900 | 6400 | 200 | n.d. | n.d.* | n.d. | n.d. | n.d. |
| U937 | 3300 | 3400 | 3100 | <20 | <20 | <20 | n.d. | n.d. | n.d. |

*n.d. = not determined h after TNF/IL-1 injection, the mice were fully protected. They remained protected 12 h after the injection. Twenty four h after pretreatment with TNF, one of the two mice died when injected with TNF+GalN, suggesting some decrease in the protective effect. Fourty eight h after pretreatment the protection had fully abated.

7. Utility and Administration

The compositions of the invention can be used for antitumor, antibacterial, antiviral or antiparasitic treatment.

Effective amounts administered to mice are for pretreatment with IL-1 in the range of between 0.5 to 25 ng per one gr of body weight of mouse and subsequent treatment (subcutaneous) with TNF in the range of 0.1 to 10 ug/g body weight, or subsequent treatment (intraperitonial) with TNF+Actinomycin-D, 4–40 ng/g and 0.5 to 1.5 μg/g respectively.

The amounts of active compound to be administered to humans will depend on various factors, such as the state of the patient, the symptoms to be treated, the severity of the affliction, the route of administration and the judgment of the prescribing physician. In the more severe cases, higher dosages of combinations of TNF and Il-1 may be considered, optionally together with interferon and/or sensitizing agent.

Administration of the IL-1 and TNF, with or without interferon, metabolic blocker, or chemotherapeutically active drug can be via any acceptable mode of administration. Treatment via injection is preferred. Known suitable modes of administration are intravenous injection, intraperitoneal, intramuscular or intralesional injection or infusion. Local treatment may be considered in case of external infections.

The compositions of the invention are prepared for administration by mixing the active materials, i.e. the IL-1, TNF, IFNs, metabolic blockers or the chemotherapeutically active drugs, with physiologically acceptable carrier, i.e. carriers which are non-toxic to recipients at the dosages and concentrations employed. For example, the carrier could be one or more of the following two materials: buffers, antioxidant, wetting or emulsifying agents, amino acids, polypeptides, proteins carbohydrates, chelating agents such as EDTA and other stabilizers and excipients.

An example for a composition according to the invention is as follows: two sterilized glass vials, vial A containing sub-deleterious amounts of IL-1 dissolved in a physiological saline solution and vial B containing therapeutically effective amounts of TNF dissolved in physiological saline. The administration of vials A and B is carried out in accordance with written instructions which accompany the two vials, the instructions indi- Legend to Table I: Effect of IL-1 on the binding of TNF, of TNF on the binding of IL-1 and of TNF and IL-1 on the binding of IFN-gamma to various cells Binding of $^{125}$I-rTNF (at 3.6 ng/ml), $^{125}$I-rIL-1 (at 49 ng/ml) and $^{125}$I-rIFN-gamma (at 13 ng/ml) to the indicated cells was determined at 40° C. as described below. Competition of IL-1 and TNF with each other for binding to their receptors was examined by applying the nonlabelled cytokines, at the indicated concentrations, simultaneously with the labelled proteins to the binding asay. The effect of pretreatment with IL-1 or TNF was examined by applying the proteins on the cells at 37° C. for 4 h prior to application of the labelled cytokines. Human TNF and IFN-gamma were radiolabelled as previously described (30, 44); the first with the chloramine T reagent to specific radioactivity of 42 Ci/g, and the second with the Bolton and Hunter reagent to specific radioactivity of 18 Ci/g. IL-1 was radioiodinated with the chloramine T reagent (31) to specific radioactivity of 40 Ci/g. Recovery of bioactivity following the iodination, as estimated by measuring the protective effect of the protein against the cytotoxicity of TNF (25) was over 95%. For determining binding of the radiolabelled proteins to SV80 (45), or HeLa (46) cells or to the FS11 strain of foreskin fibroblasts (established in the laboratory), these cells were seeded in growth medium (Eagle's minimal essential medium containing 10% fetal calf serum) into 18 mm tissue culture plates, at a density of $2.5 \times 10^5$ cells/plate. Following 24 h incubation at 37° C., the plates were transferred to ice, the growth medium removed and the radiolabelled proteins applied, in duplicates, either alone or in the presence of 1000-fold excess of the nonlabelled protein, in 150 ul growth medium also containing 20 mM Hepes buffer and 15 mM sodium azide. The nonadherent U937 cells (47) were incubated with the labelled TNF in samples of $5 \times 10^5$ cells in tubes under otherwise identical conditions. Following 2 h incubation, with constant agitation, at 4° C., the FS11 and HeLa cells were rinsed 3 times with a buffer containing 140 mM NaCl, 1.5 mM KH$_2$PO$_4$, 8 mM Na$_2$HPO$_4$, 2.7 mM KCl, 0.5 mM MgCl$_2$, 0.9 mM CaCl$_2$, 0.5% bovine serum albumin and 15 mM sodium azide (PBS/BSA). The cells were then detached in Ca$^{2+}$ and Mg$^{2+}$ free PBS containing 5 mM ethylene diamine tetraacetic acid and transferred to counting tubes for determining their associated label. SV80 cells were found to detach from the substrate in cold, therefore, following incubation with the labelled proteins they were transferred to tubes, washed 3 times by spinning, each time, for 10 mins, at 250 g and resuspending in 5 ml PBS/BSA and then transferred to counting tubes. U937 cells were washed in the same way. Nonspecific binding of the radiolabelled TNF and IL-1, observed in the presence of an excess of the non-labelled cytokines were as follows: In SV80 cells 200 and 200 CPM, in FS11 cells 300 and 200 CPM, in HeLa cells 700 and 500 CPM and in the U937 cells 600 and 200 CPM for the labelled TNF and IL-1 respectively. Non specific binding of IFN-gamma was 300 CPM in SV80 cells and 600 CPM in the FS11 cells. Specific binding was calculated by subtracting the values of nonspecific binding from the binding observed with the labelled cytokines alone. Intraduplicate variation in binding was in the range of 10% of the average value.

TABLE II

Protective effect of IL-1 and of TNF against the cytotoxicity mediated by TNF in presence of CHI, emetine and actinomycin D.

| | CELL VIABILITY upon treatment with TNF (500 U/ml) | | | | | |
|---|---|---|---|---|---|---|
| | in absence of TNF | no pre-treatment | | pretreatment with | | |
| | | | | TNF (20 U/ml) | | IL-1 (2 U/ml) |
| sensitizing agent | $OD_{540}$ | $OD_{540}$ | % | $OD_{540}$ | % | $OD_{540}$ | % |
| — | 0.305 | 0.319 | 105 | 0.308 | 101 | 0.293 | 96 |
| cycloheximide (50 μg/ml) | 0.226 | 0.020 | 9 | 0.195 | 86 | 0.163 | 72 |
| emetine (10 μg/ml) | 0.262 | 0.029 | 11 | 0.234 | 89 | 0.220 | 84 |
| actinomycin D (5 μg/ml) | 0.243 | 0.052 | 21 | 0.236 | 97 | 0.215 | 88 |

SV-80 cells following 4 h pretreatment with IL-1 or TNF or without such pretreatment were tested for their vulnerability to the cytolytic effect of TNF applied for 12 h together with the indicated sensitizing agents. Viability of the cells is presented as neutral red uptake ($OD_{540}$) and, in cultures with TNF, percentagewise as compared to the viability in cultures incubated with the sensitizing agent alone.

TABLE III

Decrease of TNF receptor expression by human peripheral blood leukocytes in response to IL-1

| IL-1 applied (U/ml) | TNF binding to: | |
|---|---|---|
| | Granulocytes | Mononuclear leukocytes (LPM) |
| 0 | 520 | 1162 |
| 0.01 | 510 | n.d. |
| 0.1 | 280 | n.d. |
| 1 | 305 | 1000 |
| 10 | 284 | 900 |
| 100 | 236 | 700 | n.d.-not determined

Granulocytes and mononuclear leukocytes were isolated from freshly collected blood by spinning through a "Monopoly" cushion. They were then incubated for 1 hr at 37° C. in a Dulbecco's modified Eagle's medium containing 10% fetal calf serum and IL-1 at the indicated concentration. Binding the $^{125}$I-labelled TNF to aliquots of $10^6$ leukocytes was then determined. As shown in the table, a significant decrease in TNF receptor expression by granulocytes was found to be induced with as little as 0.1 U/ml (LAF activity) of IL-1.

References

1. Aggarwal, B. D. et al. J. Biol. Chem. 260, 2345-2354 (1985).
2. Lomedico, P. T. et al. Nature 312, 458-462 (1984).
3. Auron, P. E. et al. Proc. natn. Acad. Sci. U.S.A. 81, 7907-7911 (1984).
4. Cameron, P. et al. J. Exp. Med. 162, 790-801 (1985).
5. March, C. et al. Nature 315, 641-647 (1985).
6. Van Damme, J. et al. Nature 314, 266-268 (1985).
7. Granger, G. A. & Kolb, W. P. J. Immunol. 101, 111-120 (1968).
8. Ruddle, N. H. & Waksman, B. H. J. Exp. Med. 128, 1267-1279 (1968).
9. Carswell, E. A. et al. Proc. natn. Acad. Sci. U.S.A. 72, 3666-3670 (1975).
10. Wallach, D. in Interferon 7 (ed. Gresser, I.) (Academic Press, London) 89-124 (1986).
11. Sugarman, B. J. et al. Science 230, 943-945 (1985).
12. Schmidt, J. A., Mizel, S. B., Cohen, D. & Green, I. J. Immunol. 128, 2177-2182 (1982).
13. Dayer, J. M., Beutler, B. & Cerami, A. J. Exp. Med. 162, 2163-2168 (1985).
14. Dayer, J. M., Zavadil-Grob, C., Ucla, C. & March, B. Eur. J. Immunol. 14, 898-901 (1984).
15. Kohase, M. et al. Cell, in press (1986).
16. Content, J. et al. Eur. J. Biochem. 152, 253-257 (1985).
17. Reutler, B. A. et al. J. Exp. Med. 161, 984-995, (1985).
18. Beutler, B. A., & Cerami, A. J. Immunol. 135, 3969-3971 (1985).
19. Bertolini, D. R. et al. Nature 319, 516-518 (1986).
20. Dewhirst, F. E., Stashenko, P. P., Mole, J. E. & Tsurumachi, T. J. Immunol. 135, 2562-2568 (1985).
21. Gamble, J. R., Harlan, J. M., Klebanoff, S. J. & Vadas, M. A. Proc. natn. Acad. Sci. U.S.A. 82, 8667-8671 (1985).
22. Schleimer, R. P. & Rutledge, B. K. J. Immunol. 136, 649-654 (1986).
23. Pober, J. S. et. al. J. Immunol. 136, 1680-1687 (1986).
24. Onozaki, K., Matsushima, K., Aggarwal, B. B. & Oppenheim. J. J. J. Immunol. 135, 3962-3968 (1985).
25. Munson, P. J. & Robard, D. Anal. Biochem. 107, 220-239 (1980).
26. Kull, F. C., Jacobs, S. & Cuatrecasas, P. Proc. natn. Acad. Sci. U.S.A. 82, 5756-5760 (1985).
27. Tsujimoto, M., Yip, Y. K. & Vilvcek, J. Proc. natn. Acad. Sci. U.S.A. 82, 7626-7630 (1985).
28. Aggarwal, B. B., Eessalu, T. F. & Hass, P. E. Nature 318, 665-667 (1985).
29. Baglioni, C., McCandless, S., Tavernier, J. & Fiers, W. J. Biol. Chem. 260, 13395-13397 (1985).
30. Israel, S., Hahn, T., Holtmann, H. & Wallach, D. Immunol. Letter, 12 217-227 (1986).
31. Dower, S. K. et al. J. Exp. Med. 162, 501-515 (1985).
32. Matsushima, K., Akahoshi, T., Yamada, M., Furutani, Y. & Oppenheim, J. J. Fed. proc. Fed. Am. Soc. Ex. Biol. 45, 620 (Abstr. 2708) (1986).
33. Tsujimoto, M., Yip, Y. K. & Vilvcek, J. J. Immunol. 136, 2441-2444 (1986).
34. Ruggiero, V., Tavernier, J., Fiers, W. & Baglioni, C. J. Immunol 136, 2445-2450. (1986).
35. Ramadori, G., Sipe, J. D., Dinarello, C. A., Mizel, S. B. & Cotton, H. R. J. Exp. Med. 162, 930-942 (1985).
36. May, W. S., Jacobs, S. & Cuatrecasas, P. Proc. natn. Acad. Sci. U.S.A. 81, 2016-2020 (1984).
37. Kelleher, D. J., Pessin, J. E. Ruoho, A. E. & Johnson, G. L. Proc. natn. Acad. Sci. U.S.A. 81, 4316-4320 (1984).
38. Iwashita, S. & Fred. Fox. C. J. Biol. Chem. 259, 2559-2567 (1984)
39. Cochet, C., Gill, G. N., Meisenhelder, J., Cooper, J. A. & Hunter, T. J. Biol. Chem. 259, 2553-2558 (1984).

40. Davis, R. J. & Czech, M. P. J. Biol. Chem. 259, 8545–8549 (1984).
41. Takayama, S., White, M. F., Lauris, V. & Kahn, R. C. Proc. natn. Acad. Sci. U.S.A. 81, 7797–7801 (1984).
42. Leeb-Lundberg, L. M. F. et al. Proc. natn. Acad. Sci. U.S.A. 82, 5651–5655 (1985).
43. Hahn, T. et al. Proc. natn. Acad. Sci. U.S.A. 82, 3814–3818 (1985)
44. Orchansky, P., Rubinstein, M. & Fischer, D. G. J. Immunol. 136, 169–173 (1986).
45. Todaro, J. G., Green, H. & Swifl, M. R. Science 153, 1252–1254 (1966)
46. Gey, G. O., Coffman, W. D. & Kubicek, M. T. Cancer Res., 12, 264–265 (1952).
47. Sundstrom C. & Nilsson, K. Int. J. Cancer 17, 565–577 (1976).
48. Aderka, D., H. Holtmann, L. Toker, T. Hahn and D. Wallach. J. Immunol. 136, 2938–2942 (1986).
49. Matsushima, K., S. K. Durum, E. S. Kimball and J. J. Oppenheim. Cell. Immunol. 92, 290 (1985).
50. Wallach, D., J. Immunol. 132: 2464 (1984).

We claim:

1. A method of reducing the lethality of TNF and/or IL-1 in a mammal which comprises administering to said mammal a sub-deleterious amount of TNF and/or IL-1 prior to administering a therapeutically effective amount of TNF and/or IL-1.

2. A method according to claim 1 wherein the TNF is recombinant TNF.

3. A method according to claim 1 wherein the IL-1 is recombinant IL-1.

4. A method according to claim 1 which comprises administering a sub-deleterious amount of TNF.

5. A method according to claim 1 which comprises administering a sub-deleterious amount of IL-1.

6. A method according to claim 1 which comprises administering a sub-deleterious amount of TNF and IL-1.

7. A method according to claim 4, 5 or 6 wherein the therapeutically effective material administered is TNF.

8. A method according to claim 4, 5 or 6 wherein the therapeutically effective material administered is IL-1.

9. A method according to claim 4, 5 or 6 wherein the therapeutically effective material administered is TNF and IL-1.

10. A method according to claim 1 wherein the therapeutically effective amount of TNF and/or IL-1 is administered in combination with an effective amount of a sensitizing agent selected from the group consisting of actinomycin-D and D-galactosamine.

11. A method according to claim 1 further comprising administering an effective amount of an interferon.

* * * * *